US010632053B2

United States Patent
Nöcker et al.

(10) Patent No.: US 10,632,053 B2
(45) Date of Patent: *Apr. 28, 2020

(54) PROCESS FOR BLEACHING HAIR

(71) Applicant: KAO GERMANY GMBH, Darmstadt (DE)

(72) Inventors: Bernd Nöcker, Darmstadt (DE); Anja Aechtner, Darmstadt (DE); Peter Bauer, Darmstadt (DE); Steven Breakspear, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 1 day.

This patent is subject to a terminal disclaimer.

(21) Appl. No.: 15/757,822

(22) PCT Filed: Mar. 15, 2016

(86) PCT No.: PCT/EP2016/055588
§ 371 (c)(1),
(2) Date: Mar. 6, 2018

(87) PCT Pub. No.: WO2017/041908
PCT Pub. Date: Mar. 16, 2017

(65) Prior Publication Data
US 2018/0353404 A1 Dec. 13, 2018

(30) Foreign Application Priority Data

Sep. 8, 2015 (EP) .................... 15184313

(51) Int. Cl.
| A61K 8/362 | (2006.01) |
|---|---|
| A61Q 5/08 | (2006.01) |
| A61K 8/22 | (2006.01) |
| A61K 8/23 | (2006.01) |
| A61K 8/35 | (2006.01) |
| A61K 8/44 | (2006.01) |
| A61K 8/73 | (2006.01) |
| A61K 8/898 | (2006.01) |

(52) U.S. Cl.
CPC ............... *A61K 8/362* (2013.01); *A61K 8/22* (2013.01); *A61K 8/23* (2013.01); *A61K 8/355* (2013.01); *A61K 8/44* (2013.01); *A61K 8/73* (2013.01); *A61K 8/898* (2013.01); *A61Q 5/08* (2013.01); *A61K 2800/4322* (2013.01); *A61K 2800/48* (2013.01); *A61K 2800/522* (2013.01); *A61K 2800/524* (2013.01); *A61K 2800/882* (2013.01)

(58) Field of Classification Search
CPC . A61K 8/362; A61K 8/73; A61K 8/23; A61K 8/355; A61K 8/44; A61K 8/898; A61K 8/22; A61K 2800/524; A61K 2800/882; A61K 2800/4322; A61K 2800/48; A61K 2800/522; A61Q 5/08
See application file for complete search history.

(56) References Cited

U.S. PATENT DOCUMENTS

2015/0034119 A1* 2/2015 Pressly .................... A61Q 5/10
132/286
2015/0037270 A1 2/2015 Pressly et al.

FOREIGN PATENT DOCUMENTS

| DE | 10 2012 212127 A1 | 1/2014 |
|---|---|---|
| EP | 1 759 685 A1 | 3/2007 |
| EP | 2 191 812 A1 | 6/2010 |
| WO | 2015/017768 A1 | 2/2015 |

OTHER PUBLICATIONS

International Search Report dated May 12, 2016, dated May 25, 2016.

* cited by examiner

*Primary Examiner* — Snigdha Maewall
(74) *Attorney, Agent, or Firm* — Norris McLaughlin, P.A.

(57) ABSTRACT

The present invention relates to a hair bleaching process for improved and milder bleaching, especially for bleaching human hair. The ready-to-use bleaching composition comprises carboxylic acids in addition to bleaching persalts and oxidizing agents added at the time of use.

15 Claims, No Drawings

PROCESS FOR BLEACHING HAIR

This application is the U.S. National Stage of International Application No. PCT/EP2016/055588, filed Mar. 15, 2016, which claims foreign priority benefit under 35 U.S.C. § 119 of European Application No. 15184313.3 filed Sep. 8, 2015 the disclosures of which are incorporated herein by reference.

The present invention relates to a hair bleaching process for improved and milder bleaching of hair, especially human hair.

Bleaching human hair involves application of a strongly oxidative composition onto hair and leaving it for a certain period of time, usually at elevated temperatures, in order to oxidatively destroy the hair's natural melanin to lighten and/or completely remove the natural hair color. Since the process involves the use of strong oxidative compositions, the hair fiber itself is also affected by such treatment and therefore the hair loses its certain natural properties such as its strength against breaking, its natural elasticity, its natural shine and natural soft feel upon touching.

Moreover, the to be bleached hair is not always homogeneous in its physicochemical status as it may be damaged due to previous chemical treatments such as dyeing and/or permanently shaping and/or environmental effects. This often leads to inhomogeneous bleach performance and therefore consumers' dissatisfaction. Therefore, there is a great need for milder and more effective bleaching compositions which overcome one or more of the above mentioned problems.

Recently, in a series of patent applications (US2015/0034119, US2015/0037270, WO2015/017768) methods are published which claim benefits of the combined use of a bismaleate based binding agent in hair chemical treatments such as oxidative hair dyeing, permanently shaping and bleaching for improving hair structure. The publications are silent on the core of the present invention.

After a long research and careful considerations of the consumers' needs, the inventors of the present invention have unexpectedly found out that when commonly used bleaching compositions are mixed with another composition comprising predominantly carboxylic acids, the damage conferred to hair is reduced while its shine is improved in comparison to a standard bleaching process.

Therefore, the first object of the present invention is a process for bleaching hair, especially human hair, wherein the compositions A, B and C are being kept separately until application onto hair, and are mixed immediately before application onto hair at a weight ratio of A:B:C in the range from 1:2:0.1 to 1:1:1 to obtain a ready-to-use composition, wherein the composition A is an anhydrous composition comprising one or more persalts and one or more alkalizing agents,
wherein the composition B is an aqueous composition comprising one or more oxidizing agents, preferably hydrogen peroxide, preferably at a concentration in the range of 1% to 30% by weight, calculated to the total of the composition, and has a pH in the range from 1.5 to 5,
wherein the composition C comprises
i) one or more carboxylic acids having three or more carboxyl groups and/or their salts, and
ii) one or more additional organic acid and/or their salts having one or two carboxyl groups,
wherein the composition C comprises the acids of i) and ii) and/or their salts of at a total concentration of 10% to 100% by weight calculated to the total of the composition C,
wherein the ready-to-use composition has an alkaline pH in the range of 8 to 11 and comprises the acids and/or their salts at a total concentration in the range of 1% to 10% by weight, calculated to the total of the ready-to-use composition,
wherein the ready-to-use composition is applied onto hair and left on the hair for a period of 1 to 45 min and rinsed off from hair and optionally the hair is washed with a cleansing composition and dried.

The second object is a kit for hair, especially human hair, comprising the compositions A, B and C as defined above to obtain the ready-to-use composition.

The term anhydrous means that the composition does not comprise any added water. It should be noted that one or more ingredients of the anhydrous composition may comprise bound crystal water or residual moisture which is not covered by the term.

The anhydrous composition A comprises one or more persalts. Useful are sodium persulfate and potassium persulfate and ammonium persulfate, earth alkali peroxides such as magnesium peroxide, melamine peroxide or urea peroxide or phthalimidoperoxy hexanoic acid. The preferred persalts are sodium persulfate and potassium persulfate. The persalt is comprised in the composition A at a total concentration in the range of 10% to 80%, preferably 15% to 70%, more preferably 20% to 60% and most preferably 25% to 60% by weight, calculated to the total of the composition A.

According to the invention, the anhydrous composition preferably comprises 0.1% to 10% by weight, calculated to the total of the composition A, one or more ammonium salts. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. The compositions may also comprise mixtures of ammonium salts.

Preferred thereof are the ammonium phosphates, such as ammonium dihydrogen phosphate, diammonium hydrogen phosphate, diammonium sodium phosphate, ammonium sodium hydrogen phosphate or ammonium disodium phosphate, ammonium chloride, ammonium sulfate and diammonium hydrogen citrate.

The anhydrous composition comprises one or more alkalizing agent(s). The preferred alkalizing agent is sodium metasilicate which is preferably comprised at a concentration from 1% to 20% by weight calculated to the total of the composition A.

The composition B is an aqueous composition and comprises one or more oxidizing agent(s). The oxidizing agents suitable are hydrogen peroxide, urea peroxide, melamine peroxide or perborate salts. The most preferred is hydrogen peroxide. The composition B comprises one or more oxidizing agents at a total concentration of 1% to 20% by weight, preferably 2% to 15%, more preferably 2% to 12% and most preferably 3% to 12% by weight, calculated to total of the composition B. The composition B may be in the form of a solution, thickened gel or an emulsion. Emulsion form is particularly preferred.

The composition C comprises
i) one or more carboxylic acids having three or more carboxyl groups and/or their salts, and
ii) one or more additional organic acid and/or their salts having one or two carboxyl groups.

Suitable carboxylic acids with three or more carboxyl groups and/or their salts are citric acid, ethylenediamine tetraacetic acid (EDTA), pyromellitic acid and glutamate diacetate. The ethylenediamine tetraacetic acid (EDTA) and/or its salts such as monosodium, disodium, trisodium and tetrasodium salts are the most preferred ones.

Suitable organic acids with one or two carboxyl groups and/or their salts are acetic acid, malic acid, lactic acid, glycolic acid, tartaric acid, formic acid, oxalic acid, malonic acid, succinic acid, glutaric acid, adipic acid, maleic acid, and fumaric acid. In the preferred embodiment of the present invention the composition C comprises as the second acid one or more organic acids having one or two carboxyl groups and the most preferred acid is malic acid and/or its salts such as sodium, potassium and ammonium salts.

The composition C comprises the two acids at a total concentration in the range of 10% to 100% by weight, preferably 12.5% to 90%, more preferably 12.5% to 75% by weight and most preferably 12.5% to 60% by weight, calculated to the total of the composition C.

The two acids are comprised in the composition C at a weight ratio of first acid (i) to second acid (ii) in the range from 10:1 to 1:250, preferably from 5:1 to 1:150, and more preferably from 2:1 to 1:100 and most preferably 1:50.

The composition C may be in the form of a powder, a dispersion, an emulsion or a solution. In a preferred embodiment of the present invention the composition C is an aqueous composition and preferably has a pH in the range of 1 to 5, preferably 2 to 4, more preferably in the range of 2.5 to 3.6. In the case that the pH must be adjusted to a certain value, the composition C comprises one or more alkalizing agents, preferably selected from ammonia, alkyl- or alkanolamines according to the general structure

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, wherein the alkalizing agents preferably selected from ammonia, monoethanolamine, and aminomethyl-propanol, and particularly suitable one is aminomethyl-propanol.

The alkalizing agent is comprised in the composition C at a total concentration in the range of 1% to 20%, preferably 1% to 17.5%, more preferably 2% to 15% and most preferably 2.5% to 13% by weight calculated to the total of the composition C.

In a further preferred embodiment of the present invention, the composition C comprises one or more thickening polymers selected from anionic, nonionic, cationic and amphoteric polymers, preferably selected from polymers with a viscosity of at least 500 mPa·s measured at a polymer concentration of 1% by weight in water and at 20° C. with a Brookfield viscometer, such as at 10 rpm for 1 minute, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, and polymeric anionic thickener such as Carbomer and its derivatives. The particularly preferred thickening polymer is dehydroxanthan gum. The thickening polymer is preferably comprised in the composition C at a total concentration in the range of 0.1% to 5%, preferably, 0.2% to 3%, more preferably 0.25% to 2.5% and most preferably 0.3% to 2% by weight calculated to the total of the composition C.

In another preferred embodiment of the present invention the composition(s) A and/or C comprise(s) one or more hair direct dyes. Suitable ones are cationic, anionic and nitro dyes. Plant dyes are also suitable for the compositions of the present invention.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, HC Blue 18, HC Red 18 and HC Yellow 16 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18 and HC Yellow 16.

Suitable cationic dyes are in principal those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17, and Basic Orange 31. The most preferred ones are Basic Red 51, Basic Yellow 87 and Basic Orange 31 sold by BASF, and HC Blue 17.

Suitable nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

The compositions A and/or C may comprise(s) one or more hair direct dye at a total concentration of 0.01% to 10%, preferably 0.05% to 7.5% and more preferably 0.1% to 5% by weight calculated to the total of each composition A or C. The composition can also comprise mixtures of several direct dyes i.e. anionic, cationic and/or nonionic ones. In such a case the dyes may be mixed at any ratio with each other.

The pH of the ready to use composition obtained by mixing the compositions A, B, and C is in the range of 8 to 11, preferably 9 to 10.5, more preferably 9.5 to 10.5.

Any of the compositions A, B, and/or C may comprise one or more of the commonly used hair conditioning compounds. These compounds are for example fatty alcohols, surfactants such as anionic, nonionic, cationic and amphoteric ones, ubiquinones, ceramides, organic solvents, lipophilic ingredients such as vegetable oils, mineral oils, silicones, fatty acid fatty alcohol esters, preservatives, amino acids, and polyols. It should be noted that these compounds are optionally comprised in any of the compositions and their incompatibility must be carefully considered prior to addition into the compositions.

Any of the compositions may comprise one or more fatty alcohols. In particular the compositions B and C may be aqueous compositions and may further be in the form of an emulsion and then comprise preferably one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, behenyl alcohol and cetostearyl alcohol.

The total concentration of fatty alcohol is in the range from 0.5% to 20%, preferably 1% to 15% by weight, calculated to total of each composition.

Compositions A, B, and C according to the present invention may comprise surfactants selected from anionic, nonionic, amphoteric and/or cationic surfactants. The anionic, nonionic, amphoteric surfactants are used generally as emulsifier or solubilizer whereas the cationic surfactants are at the same time particularly used as hair conditioners.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further surfactants suitable are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic acid esters, lauric acid esters, myristic acid esters, or palmitic acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Suitable cationic surfactants are according to the general structure

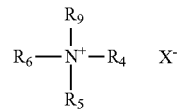

where $R_5$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or

or

where $R_7$, $R_8$ and n are same as above.

$R_9$ and $R_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The concentration of one or more total surfactants in any of the compositions A, B or C is in the range of 0.1% to 20%, preferably 0.2% to 15% and most preferably 0.2% to 10% by weight, calculated to the total of each composition.

The compositions A, B or C may further comprise lipophilic ingredients such as vegetable oils, for example, jojoba oil or any other; liquid paraffins, especially paraffinum perliquidum and parafiinum subliquidurn, silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; fatty acid esters such as octyl palmitate, isocetyl palmitate, isopropyl palmitate and octyl stearate, $C_{10}$- to $C_{36}$-fatty acid triglycerides, as well as their mixtures. Total concentration of these lipophilic compounds is in the range of 0.1% to 20% by weight, preferably from 1% to 15% by weight, and more preferably from 2% to 10% by weight, calculated to total of each composition.

Composition A, B or C can also comprise cationic polymers as conditioning and/or thickening agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

The total concentration of cationic polymers may be in the range of 0.1-7.5% by weight, preferably 0.3-5% by weight and more preferably 0.5-2.5% by weight, calculated to total of each composition Composition A, B or C may comprise one or more ceramide compound, such as the one according to general formula

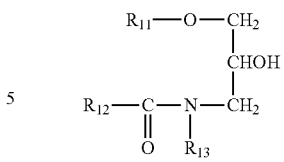

where $R_{11}$ and $R_{12}$ are independent from each other an alkyl- or alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01% to 2%, preferably 0.01% to 1% by weight calculated to the total of each composition.

The compositions A, B and/or C may comprise ubiquinone of the formula:

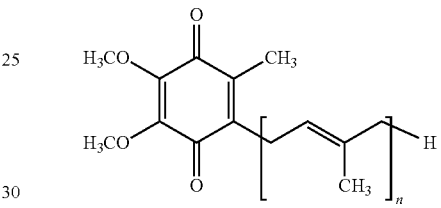

wherein n is a number from 1 to 10. Concentration of ubiquinone can vary between 0.001% and 10% by weight, calculated to the total of each composition.

The compositions A, B and/or C may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Concentration of one or more organic solvent is in the range of 0.1% to 15%, preferably 0.5% to 12.5% and more preferably 1% to 10% and most preferably 1% to 7.5% by weight calculated to the total of each composition.

The compositions A, B and/or C may further comprise one or more amino acids, preferably at a concentration in the range of 0.01% to 5%, preferably 0.1% to 3% and more preferably 0.2% to 2.5% and most preferably 0.25% to 2% by weight calculated to the total of each composition. Suitable ones are all of the known amino acids such as arginine, alanine, asparagine, glutamine, glycine, histidine, leucine, lysine, methionine, phenylalanine, prolin, serine, threonine, tryptophan, tyrosine and valin.

The compositions A, B and/or C may further comprise one or more polyol(s), preferably at a concentration in the range of 0.01% to 5%, preferably 0.1% to 3% and more preferably 0.2% to 2.5% and most preferably 0.25% to 2% by weight calculated to the total of each composition. Suitable ones are propylene glycol, diproplylene glycol, glycerine, panthenol and its derivatives.

The compositions A, B and/or C may further comprise any known preservatives if necessary.

The following examples are to illustrate the invention, but not to limit it.

EXAMPLE 1

The Composition A

|  | % by weight |
| --- | --- |
| Ammonium persulfate | 21.00 |
| Potassium persulfate | 36.00 |
| Sodium metasilicate | 11.00 |
| Diatomaceous Earth | 21.00 |
| Aerosil 380 | 1.00 |
| Liquid paraffin | 10.00 |

The above composition was prepared by combining all powder components and mixing in a suitable mixer until homogeneity was reached.

The Composition B

|  | % by weight |
| --- | --- |
| Hydrogen peroxide | 9.00 |
| Cetyl stearyl alcohol | 1.70 |
| Phosphoric acid | q.s. to pH 3.0 |
| Sodium lauryl sulfate | 0.20 |
| Salicylic acid | 0.10 |
| Water | to 100.00 |

The Composition C

|  | % by weight |
| --- | --- |
| EDTA tetrasodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH value of the above composition C was 3.5±0.1.

Then above three compositions A, B and C were mixed at a weight ratio of A, B and C 1:2:0.2. The resulting composition had a pH of approximately 9.5. For shine measurements, 25 cm long Caucasian hair tresses were purchased from International Hair Importers & Products Inc., Glendale, N.Y., USA. Cysteic acid measurements were performed on 25 cm long Caucasian hair delivered from Fischbach+Miller, Laupheim, Germany. The composition was applied onto human hair and left on the hair for 30 min at ambient temperature, rinsed off from hair and the hair was shampooed with a Goldwell Dualsenses Color shampoo, rinsed with water again, and dried (inventive process).

For comparative purposes, the same steps were carried out without using the composition C. Instead of composition C the same amount of water was added. The resulting composition had a pH of approximately 9.9. The composition was applied onto human hair and left on the hair for 30 min at ambient temperature, rinsed off from hair and the hair was shampooed with a Goldwell Dualsenses Color shampoo, rinsed with water again, and dried (comparative process).

Hair shine was measured by image analysis of polarized light reflection with the SAMBA Hair system from Bossa Nova Technologies, Culver City, Calif., USA. Each hair tress was measured and analyzed for 4 times and shine values were calculated by three different mathematical methods: 1) Bossa Nova Tech (BNT), 2) Reich-Robbins analysis (RR), and 3) Textile Research Institute analysis (TRI). The method is known from a scientific publication by N. Lefaudeux et al., in Journal of Cosmetic Science, 60(2), 153-169, 2009. Higher values correspond to more shine in all types of calculations. Based on the four independent measurements, arithmetic means, standard deviations, and confidence intervals were calculated. Student's t test (2 samples, unpaired, two-tailed) was used to calculate the significance values between the two hair tresses with the same calculation method (BRT, RR, TRI). Hair tresses were dark brown and 25 cm long.

| Number of measurement | Tress 1 (inventive process) | | | Tress 2 (comparative process) | | |
| --- | --- | --- | --- | --- | --- | --- |
|  | BNT | RR | TRI | BNT | RR | TRI |
| 1 | 4.34 | 9.34 | 6.32 | 3.86 | 7.83 | 5.61 |
| 2 | 4.25 | 9.04 | 6.15 | 3.92 | 7.93 | 5.66 |
| 3 | 4.44 | 9.37 | 6.41 | 3.58 | 7.21 | 5.39 |
| 4 | 4.53 | 9.4 | 6.45 | 3.61 | 7.2 | 5.37 |
| Arithmetic mean | 4.39 | 9.29 | 6.33 | 3.74 | 7.54 | 5.51 |
| SD | 0.12 | 0.17 | 0.13 | 0.17 | 0.39 | 0.15 |
| CI | ±0.24 | ±0.33 | ±0.26 | ±0.35 | ±0.78 | ±0.30 |
| p value | <0.05 | <0.05 | <0.05 | — | — | — |

The shine measurements revealed that in all cases the tress treated with the inventive process exhibited significantly more shine compared to the state-of-the-art process, independently of the calculation method.

The amount of damage conferred to the hair was measured by cysteic acid concentration upon treatment. Cysteine residues in hair are converted to cysteic acid during chemical processing of hair such as bleaching. It is well known to the skilled in the art that the amount of cysteic acid produced in a chemical hair treatment directly corresponds to hair damage. Consequently the lower cysteic acid values upon treatment, the less damage to hair was conferred.

Cysteic acid was analyzed as described by Robbins and Kelly (J. Soc. Cosmetic Chemists, Vol. 20, p. 555-564, published on Aug. 19, 1969). In brief, hair tresses treated with the inventive process and the comparative process (without addition of composition C) were hydrolyzed by mineral acidic treatment under reflux boiling conditions. This treatment delivered free amino acids which were then analyzed by an amino acid analyzer. Hair tresses were dark brown and 25 cm long.

| Treatment group | Cysteic acid [mol/100 mol] |
| --- | --- |
| Virgin hair | 0.8 |
| Inventive process | 4.5 |
| Comparative process | 5.6 |

The results clearly show the superiority of the inventive process in terms of hair damage. The damage to hair was much lower compared to the comparative process.

In order to make sure that the above proven effects were indeed from the addition of the third composition but not from the pH change, another comparative test was carried out where the composition was added water and the pH was adjusted with a phosphoric acid solution. The values obtained from shine measurements and cysteic acid content of the hair were very similar to the values obtained with the above comparative process. Therefore, it is beyond any doubt that the effect shown above is from the addition of the third composition but not from the decrease in pH value.

Similar results were obtained with the following compositions (composition C) when used with the compositions A and B of the Example 1.

EXAMPLE 2

| Component | % by weight |
|---|---|
| AMP | 6.0 |
| EDTA tetrasodium salt | 3.0 |
| Malic acid | 13.0 |
| Lactic acid | 4.0 |
| Hydroxypropyl xanthan gum | 0.6 |
| Polyquaternium-10 | 0.1 |
| Water | to 100 |

The pH value of the above composition C was 3.4±0.1.

EXAMPLE 3

The Composition C

| Component | % by weight |
|---|---|
| Monoethanolamine (MEA) | 2.7 |
| EDTA tetrasodium salt | 5.0 |
| Malic acid | 15.0 |
| Hydroxypropyl xanthan gum | 0.6 |
| Panthenol | 0.1 |
| Water | to 100 |

The pH value of the above composition C was 3.3±0.1.

EXAMPLE 4

The Composition C

| Component | % by weight |
|---|---|
| AMP | 6.0 |
| Citric acid | 5.0 |
| Maleic acid | 15.0 |
| Hydroxypropyl xanthan gum | 0.6 |
| Behenamidopropyl trimonium chloride | 0.2 |
| Water | to 100 |

The pH value of the above composition C was 1.4±0.1.

EXAMPLE 5

The Composition C

| Component | % by weight |
|---|---|
| MEA | 2.0 |
| Lactic acid | 15.0 |
| Citric acid | 6.0 |
| Hydroxypropyl xanthan gum | 0.6 |
| Polyquaternium-67 | 0.1 |
| Water | to 100 |

The pH value of the above composition C was 2.7±0.1.

EXAMPLE 6

The composition A

| | % by weight |
|---|---|
| Ammonium persulfate | 21.00 |
| Potassium persulfate | 36.00 |
| Sodium metasilicate | 11.00 |
| Diatomaceous Earth | 19.00 |
| Aerosil 380 | 1.00 |
| Basic red 51 | 1.00 |
| HC red 18 | 1.00 |
| Liquid paraffin | 10.00 |

The hair was treated with the above composition using the composition B and C of the Example 1 as described under Example 1. It was observed that the hair was bleached and dyed effectively into intensive red color. Exclusion of the composition C resulted in loss of color brilliance and less smooth hair feeling.

EXAMPLE 7

The composition C

| | % by weight |
|---|---|
| EDTA tetrasodium salt | 1.0 |
| Malic acid | 13.0 |
| Aminomethylpropanol | 6.0 |
| Basic red 51 | 1.00 |
| HC red 18 | 1.00 |
| HC Blue 18 | 0.1 |
| HC Yellow 16 | 0.1 |
| Hydroxypropyl xanthan gum | 0.6 |
| Cetrimonium chloride | 0.1 |
| Preservative | q.s. |
| Water | to 100 |

The pH value of the above composition C was 3.5±0.1.

The hair was treated with the above composition C using the compositions A and B of the Example 1 as described under the Example 1. It was observed that the hair was bleached and dyed effectively into intensive red color. Exclusion of the composition C resulted in loss of color brilliance and less smooth hair feeling.

EXAMPLE 8

The Composition C (Powder)

| EDTA tetrasodium | 7.0 |
|---|---|
| Malic acid | 93.0 |

1 g of the above composition was added to the mixture of 10 g of Composition A and 20 g of composition B (1 to 2) of the Example 1. After mixing thoroughly, the resulting composition was applied onto hair and rinsed off after leaving on the hair for 30 min. It was observed that the hair was effectively bleached.

EXAMPLE 9

The Composition C

|  | % by weight |
| --- | --- |
| EDTA monosodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 | pH of the above composition C is approximately 3.1.

EXAMPLE 10

The Composition C

|  | % by weight |
| --- | --- |
| EDTA disodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 | pH of the above composition C is approximately 3.2.

EXAMPLE 11

The Composition C

|  | % by weight |
| --- | --- |
| EDTA trisodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 | pH of the above composition C is approximately 3.4.

The invention claimed is:

1. A process for bleaching hair, the process comprising: separately storing the compositions A, B and C before application onto hair, mixing compositions A, B and C immediately before application onto hair at a weight ratio of A:B:C in the range from 1:2:0.1 to 1:1:1 to obtain a ready-to-use composition, wherein the composition A is an anhydrous composition comprising one or more persalts and one or more alkalizing agents, wherein the composition B is an aqueous composition comprising one or more oxidizing agents, at a concentration in the range of 1% to 30% by weight, calculated to the total of the composition, and has a pH in the range from 1.5 to 5, wherein the composition C comprises
i) one or more carboxylic acids having three or more carboxyl groups and/or their salts, and
ii) one or more additional organic acid and/or their salts having one or two carboxyl groups, wherein the composition C comprises the acids of i) and ii) and/or their salts of at a total concentration of 10% to 100% by weight calculated to the total of the composition C, wherein the ready-to-use composition has an alkaline pH in the range of 8 to 11 and comprises the acids and/or their salts at a total concentration in the range of 1% to 10% by weight, calculated to the total of the ready-to-use composition;

applying the ready-to-use composition on the hair for 1 minute to 45 minutes; and rinsing the ready-to-use composition off the hair.

2. The process according to claim 1, wherein the carboxylic acid with 3 or more carboxyl groups is selected from citric acid, ethylenediamine tetraacetic acid (EDTA), pyromellitic acid and glutamate diacetate, and the organic acid with one or two carboxyl groups is selected from the group of acetic acid, malic acid, lactic acid, glycolic acid, tartaric acid, formic acid, oxalic acid, malonic acid, succinic acid, glutaric acid, adipic acid, maleic acid, and fumaric acid wherein the composition C comprises the first acid (i) and the second acid (ii) at a weight ratio (i)/(ii) in the range from 10:1 to 1:250.

3. The process according to claim 2, wherein the composition C is a powder, a dispersion, an emulsion or a solution.

4. The process according to claim 3, wherein the composition C is an aqueous composition.

5. The process according to claim 4, wherein the composition C has a pH in the range from 1 to 5, and comprises at least one alkalizing agent selected from ammonia, alkyl- or alkanolamines according to the general structure

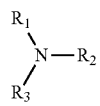

Wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H.

6. The process according to claim 2, wherein the carboxylic acid with three or more carboxyl groups is EDTA and/or its salts.

7. The process according to claim 2, wherein the organic acid with one or two carboxyl groups is malic acid and/or its salts.

8. The process according to claim 1, wherein the composition A comprises one or more persalts selected from sodium persulfate, potassium persulfate, and ammonium persulfate, or their mixture, at a concentration in the range of 10 to 80% by weight calculated to the total of composition A, and the at least one alkalizing agent is selected from sodium metasilicate, ammonium salts, carbonate salts and bicarbonate salts.

9. The process according to claim 5, wherein at least one of the composition A and composition C further comprises one or more hair direct dye, selected from the group consisting of cationic, anionic, neutral nitro dyes and their mixtures thereof.

10. The process according to claim 5, wherein at least one of the composition A, the composition B and the composition C further comprises one or more conditioning ingredients, selected from fatty alcohols, surfactants selected from anionic, nonionic, cationic and amphoteric ones, ubiquinones, organic solvents, silicones, aminated silicones, cyclic silicones, arylated silicones, antioxidants, preservatives, amino acids, and polyols.

11. The process according to claim 5, wherein the composition C further comprises one or more thickening polymers with a viscosity of at least 500 mPa·s measured at a polymer concentration of 1% by weight in water and at 20° C. with a Brookfield viscometer, with a spindle.

12. The process according to claim 11, wherein the thickening polymer is selected from dehydroxanthan gum, hydroxypropyl xanthan gum, xanthan gum, and polymeric anionic thickeners.

13. The process according to claim 10, wherein ubiquinones are selected from

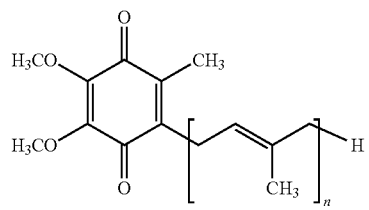

wherein n has a number from 1 to 10.

14. The process according to claim 10, wherein the aminated silicones comprise primary, secondary, tertiary or quaternary ammonium groups.

15. A kit for hair comprising the compositions A, B and C according to claim 1.

* * * * *